(12) United States Patent
Itsuji (10) Patent No.: US 8,232,526 B2
(45) Date of Patent: Jul. 31, 2012

(54) ANALYZING APPARATUS (75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/145,330

(22) PCT Filed: Jan. 22, 2010

(86) PCT No.: PCT/JP2010/000374
§ 371 (c)(1),
(2), (4) Date: Jul. 19, 2011

(87) PCT Pub. No.: WO2010/084765
PCT Pub. Date: Jul. 29, 2010

(65) Prior Publication Data
US 2011/0272579 A1 Nov. 10, 2011

(30) Foreign Application Priority Data

Jan. 23, 2009 (JP) ................................ 2009-012455
Dec. 21, 2009 (JP) ................................ 2009-288818

(51) Int. Cl.
G01J 5/02 (2006.01)
(52) U.S. Cl. .................................................... 250/341.1
(58) Field of Classification Search ............... 250/338.1, 250/339.06, 340, 341.1, 341.8, 343, 358.1
See application file for complete search history.

(56) References Cited

U.S. PATENT DOCUMENTS

2004/0130725 A1*   7/2004  Kido et al. ..................... 356/484
2006/0043298 A1*   3/2006  Kawase et al. ........... 250/339.06
2009/0097109 A1    4/2009  Akiyama et al.

FOREIGN PATENT DOCUMENTS

| EP | 1662249 A1 | 5/2006 |
| GB | 2397207 A | 7/2004 |
| JP | 2004-003902 A | 1/2004 |
| WO | 2008/065741 A1 | 6/2008 |

* cited by examiner

Primary Examiner — Mark R Gaworecki
(74) Attorney, Agent, or Firm — Canon USA, Inc., IP Division

(57) ABSTRACT

An analyzing apparatus includes a first optical unit that causes a terahertz wave generated by a generation unit to be condensed at a first position in an object; a second optical unit that causes the terahertz wave from the object to be condensed at a second position; a third optical unit that causes the terahertz wave condensed at the second position to be condensed at a third position; and a detection unit that detects the terahertz wave condensed at the third position. The analyzing apparatus selectively detects the terahertz wave from the first position in the object from among terahertz waves from the object.

5 Claims, 10 Drawing Sheets

ANALYZING APPARATUS

TECHNICAL FIELD

The present invention relates to an analyzing apparatus configured to analyze an object by using a terahertz wave.

BACKGROUND ART

A THz-time domain spectroscopy (THz-TDS) apparatus (THz-TDS is also called terahertz time domain spectroscopy) acquires the electric field intensity of a terahertz wave (in this description, terahertz waves refers to electromagnetic waves within at least a partial frequency band of a range from 0.03 to 30 THz) that reaches a detection unit by an ultrashort pulse. The electric field intensity is continuously recorded while the timing at which the ultrashort pulse reaches the detection unit is changed. Accordingly, the time waveform of the terahertz wave can be acquired. Also, when characteristic absorption of the object is measured, the object is irradiated with the terahertz wave, and the time waveform of the terahertz wave from the object is acquired. Then, the acquired time waveform is transformed by Fourier transform, so that the time waveform is converted into information of a frequency domain, and a frequency spectrum can be obtained.

If interfaces (an interface is a portion at which a refractive index changes) are present in the object, a time waveform that contains reflected waves from the interfaces in the object can be acquired. Thus, the inner structure of the object can be acquired.

At this time, an interference fringe may appear in the frequency spectrum because of the reflected waves from the interfaces. The interference fringe may become a noise when the frequency spectrum of the object is analyzed. To reduce the influence of such an interference fringe, a method is described in Japanese Patent Laid-Open No. 2004-003902 as follows. After the time waveform of the terahertz waves containing the reflected waves from the interfaces is acquired, a time waveform relating to a reflected wave from an undesirable interface is eliminated from the acquired time waveform.

CITATION LIST

Patent Literature

PTL 1: Japanese Patent Laid-Open No. 2004-003902

SUMMARY OF INVENTION

Technical Problem

Herein, information of vibration because of a reflected wave from a desirable interface (a light condensed position in the object) is also superposed on the time waveform relating to the reflected wave from the undesirable interface. Owing to this, with the method described in Japanese Patent Laid-Open No. 2004-003902, the information relating to the reflected wave from the desirable interface may be eliminated.

Solution to Problem

An analyzing apparatus configured to analyze an object by using a terahertz wave according to an aspect of the present invention includes a generation unit configured to generate the terahertz wave; a first optical unit configured to cause the terahertz wave generated by the generation unit to be condensed at a first position in the object; a second optical unit configured to cause the terahertz wave from the object to be condensed at a second position; a third optical unit configured to cause the terahertz wave condensed at the second position to be condensed at a third position; and a detection unit configured to detect the terahertz wave condensed at the third position. The analyzing apparatus is configured to selectively detect the terahertz wave from the first position in the object from among terahertz waves from the object.

Advantageous Effects of Invention

With the analyzing apparatus according to the aspect of the present invention, a terahertz wave from a desirable position in the object can be selectively detected from among terahertz waves from the object, because the intensity distributions of the terahertz waves other than the terahertz wave from the desirable interface in the object (the light condensed position in the object) are spread on the detection unit.

DESCRIPTION OF EMBODIMENTS

Figure 1:
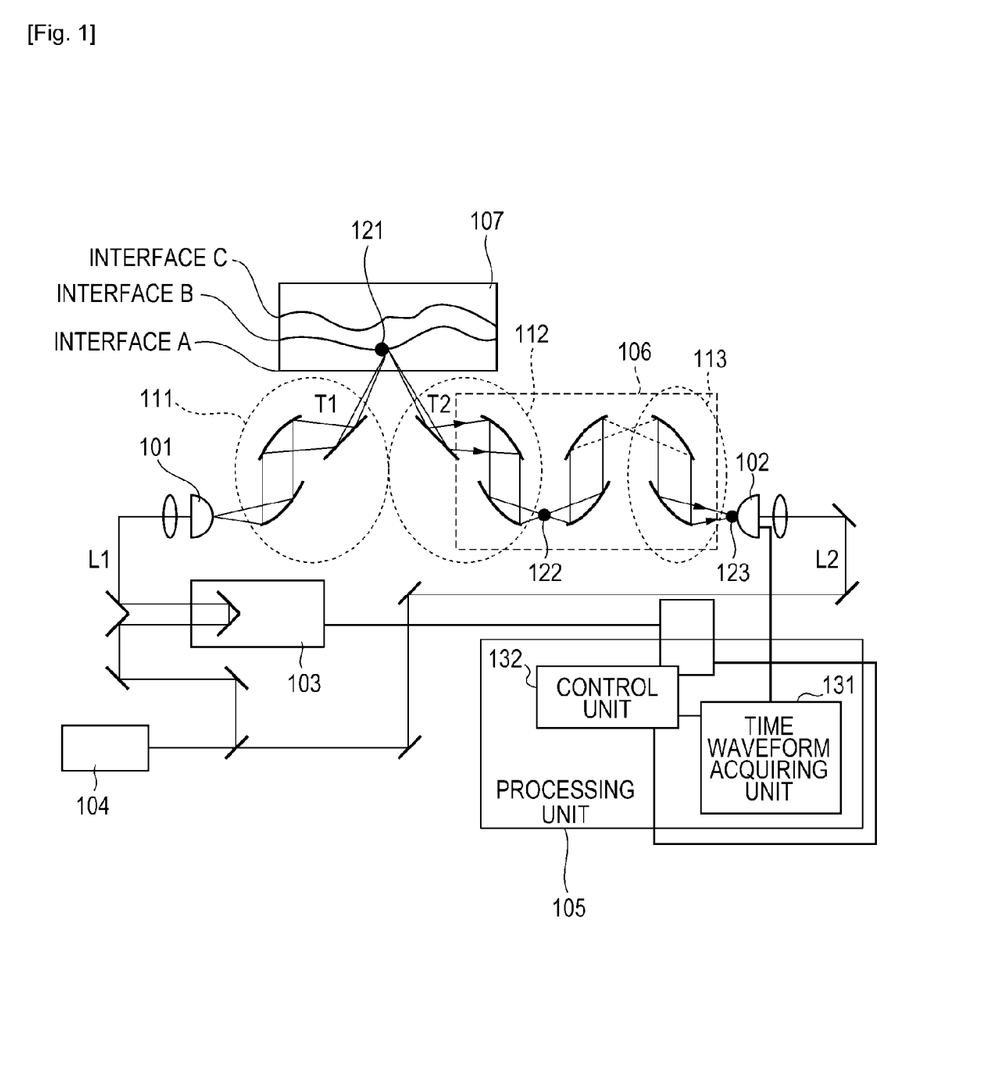
FIG. 1 is a schematic illustration explaining an apparatus configuration according to an embodiment.

An analyzing apparatus configured to analyze an object (a sample) by using a terahertz wave according to an embodiment will be described with reference to FIG. 1. FIG. 1 is a schematic illustration explaining an apparatus configuration according to this embodiment.

The analyzing apparatus includes a generation unit 101. The generation unit 101 is, for example, a photoconductive element including a photoconductive film and a pair of electrodes, the electrodes being provided in the photoconductive film with a gap interposed therebetween. A terahertz wave is generated because the gap in the photoconductive element is irradiated with pulse laser light generated from a laser source 104 and a voltage is applied to the pair of electrodes.

The analyzing apparatus includes a first optical unit 111 that causes the terahertz wave generated from the generation unit 101 to be condensed at a first position 121 (an interface B in a sample 107 shown in FIG. 1). The first optical unit 111 causes the terahertz wave to be condensed at a desirable position in the sample 107 by using a mirror or a lens.

The analyzing apparatus also includes a second optical unit 112 that causes the terahertz wave from the sample 107 to be condensed at a second position 122. The second optical unit 112 causes the terahertz wave to be condensed at a desirable position in a space by using a minor or a lens.

The analyzing apparatus further includes a third optical unit 113 that causes the terahertz wave condensed at the second position 122 to be condensed at a third position 123. In addition, the analyzing apparatus includes a detection unit 102 that detects the terahertz wave condensed at the third position 123. The third optical unit 113 causes the terahertz wave to be condensed at a desirable position on the detection unit 102 by using a minor or a lens. Hereinafter, the second optical unit 112 and the third optical unit 113 are collectively referred to as a selection unit 106.

Thus, the terahertz wave from the first position 121 in the sample 107 can be selectively detected from among terahertz waves from the sample 107, because the intensity distributions of terahertz waves other than the terahertz wave from the desirable interface in the sample 107 (a light condensed position in the sample 107) are spread on the detection unit 102. Also, with the configuration, the resolution of a frequency spectrum can be relatively increased. The resolution of the frequency spectrum is an inverse to the time length of the time waveform of the terahertz wave.

The third position 123 may be arranged on a detection surface (denoted by reference numeral 208 in FIG. 2A) of the detection unit 102. If the detection unit 102 is a photoconductive element, the third position 123 is arranged in the gap between the pair of electrodes to be located on a surface of the photoconductive film in which the pair of electrodes are provided. Accordingly, detection accuracy for the terahertz wave from the first position 121 in the sample 107 can be increased.

To perform the terahertz time domain spectroscopy, a time waveform acquiring unit 131 may be provided. The time waveform acquiring unit 131 acquires the time waveform of the terahertz wave reflected from the first position 121 in the sample 107, by using the terahertz wave detected by the detection unit 102. In this case, a delay optical unit 103 may be provided. The delay optical unit 103 can change the timing at which the terahertz wave is detected. In addition, a control unit 132 may be provided. The control unit 132 controls the delay optical unit 103 on the basis of the time domain of the time waveform (hereinafter, also referred to as measurement time domain). The control unit 132 can acquire the time waveform of the terahertz wave. The time domain may be set in accordance with the intensity of the terahertz wave that is detected by the detection unit 102. The above configuration will be described in a third embodiment. The above setting may be performed by a processing unit 105. The time waveform acquiring unit 131 and the control unit 132 may be provided in the processing unit 105, or may be provided separately from one another.

Further, an opening (denoted by reference numeral 511 in FIG. 4A) may be provided between the third optical unit 113 and the detection unit 102. The opening 511 is arranged to allow the terahertz wave, which is condensed at the third position 123 from the sample 107 from among the terahertz waves from the sample 107, to selectively pass therethrough. The above configuration will be described in a first embodiment.

First Embodiment

FIG. 1 is a brief configuration diagram showing a terahertz wave analyzing apparatus and a terahertz wave analyzing method according to a first embodiment of the present invention. Referring to FIG. 1, the analyzing apparatus includes a part that constructs the time waveform of a terahertz wave pulse in a time domain, and a selection unit 106 that selects a terahertz wave pulse.

The part that constructs the time waveform of the terahertz wave pulse in the time domain follows a basic configuration of a typical THz-TDS apparatus. In particular, the part includes a generation unit 101, a detection unit 102, a delay optical unit 103, a laser source 104, and a processing unit 105.

The generation unit 101 generates a terahertz wave pulse. A method of generating a terahertz wave by the generation unit 101 may be a method using instantaneous carrying current or a method using interband transition of a carrier. In particular, the method using the instantaneous carrying current may be a method of generating a terahertz wave by irradiating the surface of semiconductor or organic crystal with laser light, or a method in which an electric field is applied to a photoconductive element having an antenna pattern formed of a metal electrode on a semiconductor thin film, and the applied portion is irradiated with laser light. Otherwise, a PIN diode may be applied. The method using a gain structure may be a method using a semiconductor quantum well structure.

The detection unit 102 detects the electric field intensity of the terahertz wave pulse. The detecting method by the detection unit 102 may be a method of detecting current corresponding to the electric field intensity caused by photoconduction, a method of detecting an electric field by using electrooptic effect, or a method of detecting a magnetic field by using magnetooptic effect. The method of detecting the current caused by the photoconduction may be a method using a photoconductive element. The method of detecting the electric field by using the electrooptic effect may be a method using an orthogonal polarizer and electrooptic crystal. The method of detecting the magnetic field by using the magnetooptic effect may be a method using an orthogonal polarizer and magnetooptic crystal. The terahertz wave incident on the detection unit 102 is focused on the detection unit 102, so that the intensity per unit area can be increased, and the detection sensitivity can be increased.

The laser source 104 outputs ultrashort pulse laser light. The generation unit 101 and the detection unit 102 are operated when a carrier is excited with the ultrashort pulse laser light. Referring to FIG. 1, the ultrashort pulse laser light is divided into two optical paths L1 and L2. The ultrashort pulse laser light passing through the optical path L1 is input to the generation unit 101 through the delay optical unit 103, which will be described later. The ultrashort pulse laser light passing through the optical path L2 is input to the detection unit 102.

The delay optical unit 103 adjusts a sampling position of the detection unit 102 in the time waveform of the terahertz wave pulses. In particular, the ultrashort pulse laser light that is input to the generation unit 101 is adjusted so that the timing of the ultrashort pulse laser light that is input to the detection unit 102 is delayed or changed. The delay time may be adjusted by a method of directly adjusting an optical length, or a method of adjusting an effective optical length.

The directly adjusting method may be a method using a folding optical system and a movable portion. The method of adjusting the effective optical length may be a method of changing a time constant or a refractive index in a path through which a trigger signal propagates. FIG. 1 illustrates an example using the folding optical system and the movable portion.

The processing unit 105 constructs the time waveform of the terahertz wave pulse. The processing unit 105 constructs the time waveform with reference to the adjustment amount of the delay optical unit 103 and the output of the detection unit 102. To obtain the frequency spectrum, the time waveform is transformed by Fourier transform. When the THz-TDS apparatus is used as an analyzing apparatus, a change in time waveform while the sample 107 is irradiated with the terahertz wave is obtained. The processing unit 105 can visualize the sample 107 by monitoring the relative positions of the sample 107 and the terahertz wave with which the sample 107 is irradiated.

Figure 5A:
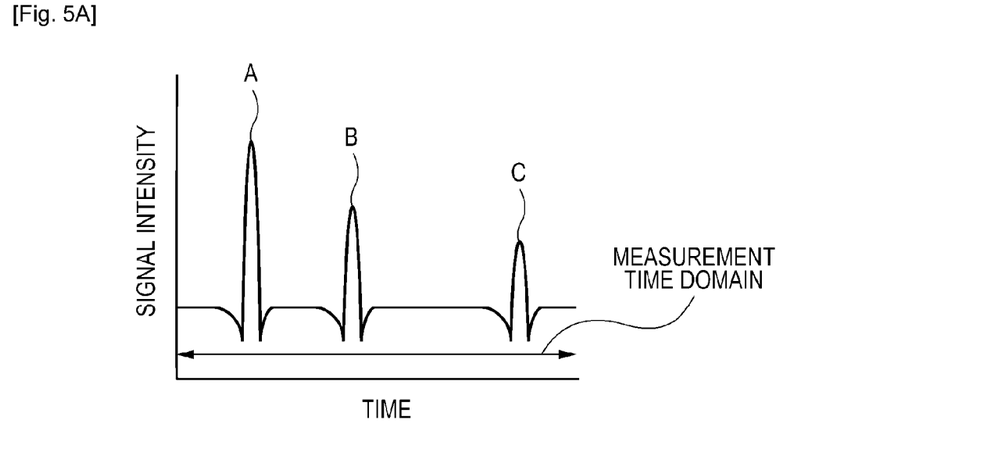
FIG. 5A is an illustration explaining an exemplary operation of a terahertz wave analyzing apparatus according to an embodiment.

The above configuration is a typical configuration of the THz-TDS apparatus. The generation unit 101 and the detection unit 102 are arranged at reflective positions relative to the sample 107. A terahertz wave pulse T1 generated by the generation unit 101 is focused at the sample 107, and part of the terahertz wave pulse T1 is absorbed and scattered depending on the property of the focused portion. Then, a terahertz wave pulse T2 reflected from the sample 107 enters the detection unit 102, and is measured. FIG. 5A is a schematic illustration showing a terahertz wave pulse to be measured by the apparatus in this state. Since a terahertz wave has a large wavelength, a band in which the terahertz wave is focused is from several submillimeters to several millimeters. In addition, since the terahertz wave has good transmissivity depending on the material of the sample 107. Thus, terahertz wave pulses reflected from positions other than the focal point can be also measured.

Figure 5B:
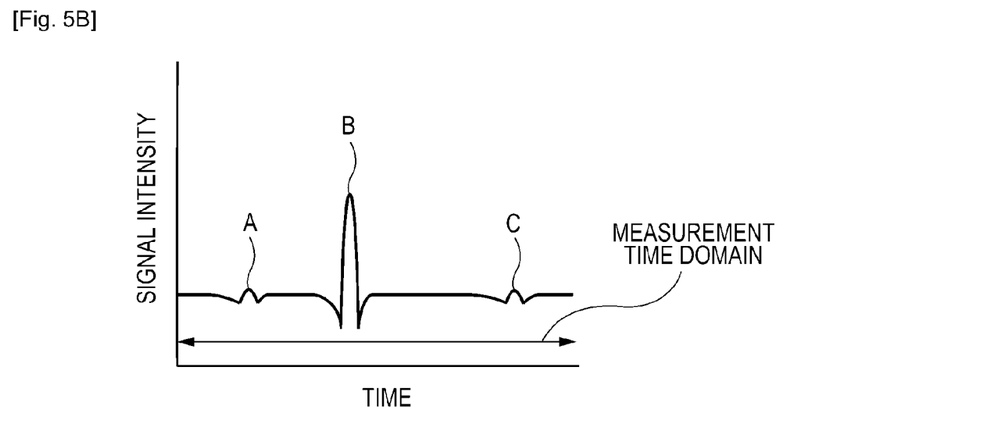
FIG. 5B is an illustration explaining an exemplary operation of a terahertz wave analyzing apparatus according to an embodiment.

When a plurality of interfaces (A, B, and C) having a plurality of refractive indices are present in the sample 107 as shown in FIG. 1, and the interfaces are present in a measurable range including a focal position, the terahertz wave pulse is measured such that the plurality of reflected pulses (corresponding to the interfaces A, B, and C) are successively arranged as shown in FIG. 5A. If the frequency spectrum is obtained in this state, an interference fringe because of the plurality of reflected pulses may be superposed on the spectrum. In this embodiment, for example, as shown in FIG. 5B, a desirable terahertz wave pulse (reflected pulse in FIG. 5B, corresponding to the interface B) is selected from among these reflected pulses, and the selected terahertz wave pulse is analyzed.

To attain such analysis, the analyzing apparatus according to this embodiment includes the selection unit 106. The selection unit 106 optically selects a terahertz wave pulse that is reflected from a focal position from among the terahertz wave pulses T2 from the sample 107. The selection unit 106 includes at least two optical systems arranged along the path of the terahertz wave pulse T2. Each optical system is formed of mirrors or lenses having a pair of curvature surfaces.

Figure 2A:
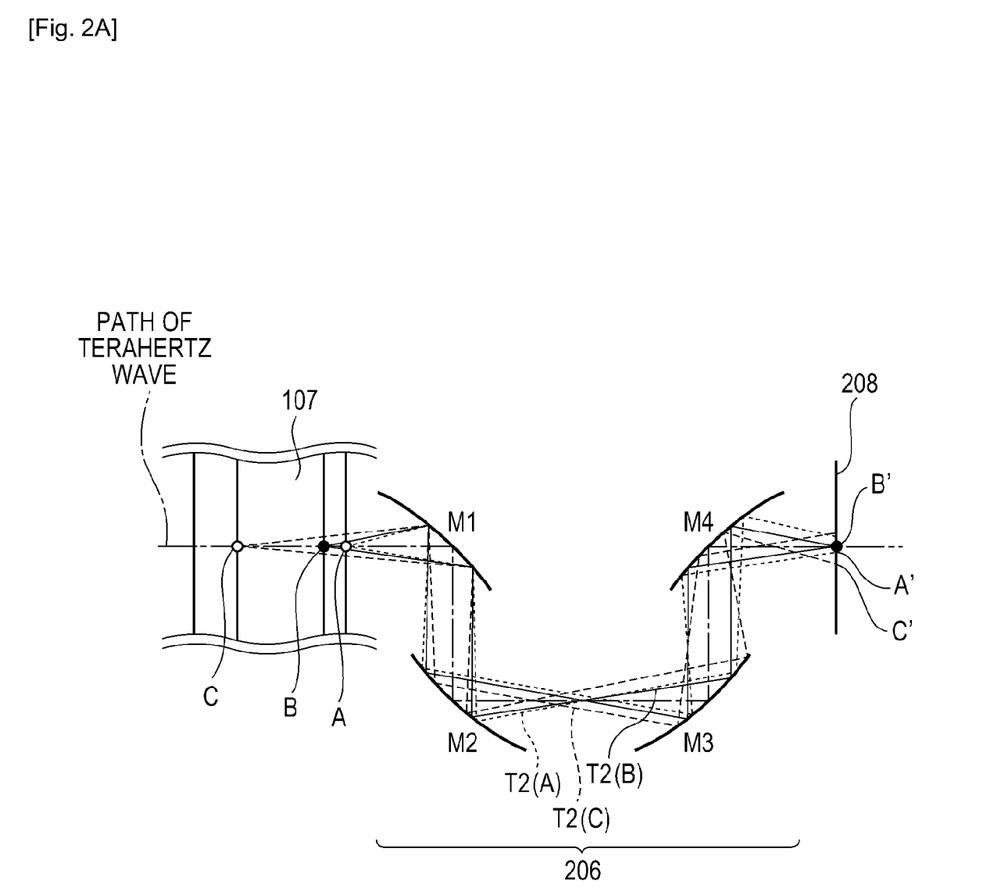
FIG. 2A is an illustration explaining an exemplary selection unit according to an embodiment.

FIG. 2A shows an example in which the selection unit 106 is formed of minors having a pair of curvature surfaces. In FIG. 2A, the configuration example of the selection unit 106 is expressed as a selection unit 206. Referring to FIG. 2A, the selection unit 206 includes four parabolic mirrors M1, M2, M3, and M4. Also, a sample 107 has interfaces A, B, and C. This example shows that the focus of the selection unit 206 is provided on the interface B. The detection unit 102 is arranged on a detection surface 208. Herein, the mirrors having the pair of curvature surfaces represent an optical system that causes light to be focused when the light is input and output like the parabolic mirrors M1, M2, M3, and M4. FIG. 2A shows the example in which the mirrors having two pairs of curvature surfaces are arranged. The path of a terahertz wave is a path through which a terahertz wave pulse passes from the focal point in the sample 107 to the detection surface 208. The minors or lenses are arranged in line along the path. With this arrangement, the focal point provided on the input side of the first pair is aligned with the focal position in the sample 107, and the focal point on the output side of the first pair is aligned with the focal point on the input side of the second pair. The focal positions are aligned with one another for the following pairs, and the focal point on the output side of the final pair is aligned with a point on the detection surface 208 of the detection unit 102.

An operation of the selection unit 206 will be described. When the minors having the pair of curvature surfaces are arranged, although the terahertz wave pulse reflected from the focal position on the interface B is focused again, for example, images of terahertz wave pulses reflected from the interfaces A and C which are located off the focal position are defocused. By successively arranging such a plurality of optical systems, the defocused state of the images may be increased. Depending on the degree of defocused state, a part of the terahertz wave pulses may be shaded by a mirror. Consequently, the image from the focal point on the interface B via the selection unit 206 is focused again at a focal point on an interface B' on the detection surface 208 whereas images on interfaces A' and C' from the interfaces A and C are projected in a defocused manner.

The detection region of the terahertz wave pulse by the detection unit 102 corresponds to the focal point of ultrashort pulse laser light that passes through the optical path L2 and focused on the detection unit 102. The detection region typically has a diameter of about several micrometers. For example, when a photoconductive element is applied to the detection unit 102, an antenna pattern is formed. The antenna pattern has a gap with a size substantially corresponding to the size of the detection region. The gap is irradiated with the ultrashort pulse laser light, a carrier is excited with the ultrashort pulse laser light, the carrier is varied due to the electric field of the terahertz wave, current is generated, and the current is detected.

When the output of the selection unit 206 is converted into the intensity of a terahertz wave pulse per unit area, the intensities of the images on the interfaces A' and C' are smaller than the intensity of the focal image on the interface B' because the images on the interfaces A' and C' are spread in a wide area. As described above, since the detection region of the detection unit 102 is small, the intensity of the terahertz wave pulse incident on the detection region varies depending on the focal position. Consequently, as shown in FIG. 5B, the signals of components reflected from positions other than the focal position on the interface B are attenuated.

Figure 2B:
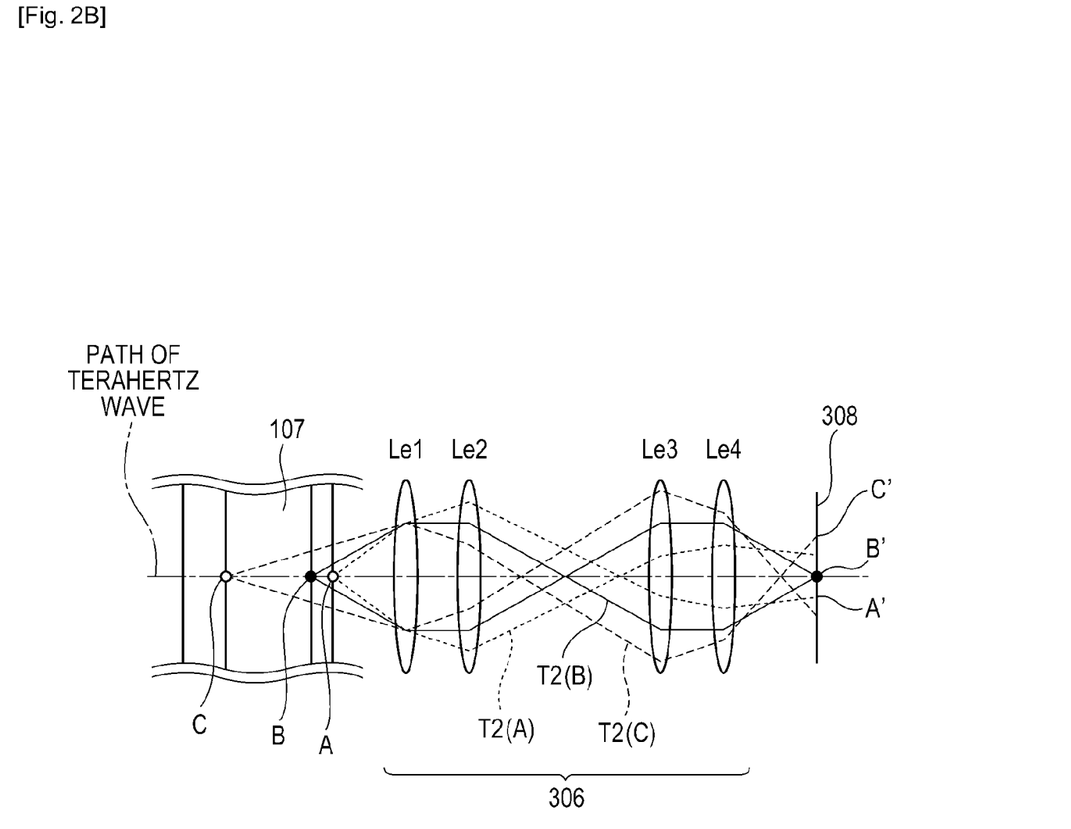
FIG. 2B is an illustration explaining an exemplary selection unit according to an embodiment.

FIG. 2B shows an example in which the selection unit 106 is formed of lenses having a pair of curvature surfaces. In FIG. 2B, the configuration example of the selection unit 106 is expressed as a selection unit 306. Reference numeral 308 denotes the detection surface of the detection unit 102. The lenses having the pair of curvature surfaces represent an optical system that causes light to be focused when the light is input and output like lenses Le1, Le2, Le3, and Le4. Herein, an example is shown in which two pairs of lenses each having a pair of curvature surfaces are arranged. With this arrangement, since the path of the terahertz wave is linear as compared with the arrangement shown in FIG. 2A, the optical axis can be more easily adjusted.

Figure 3A:
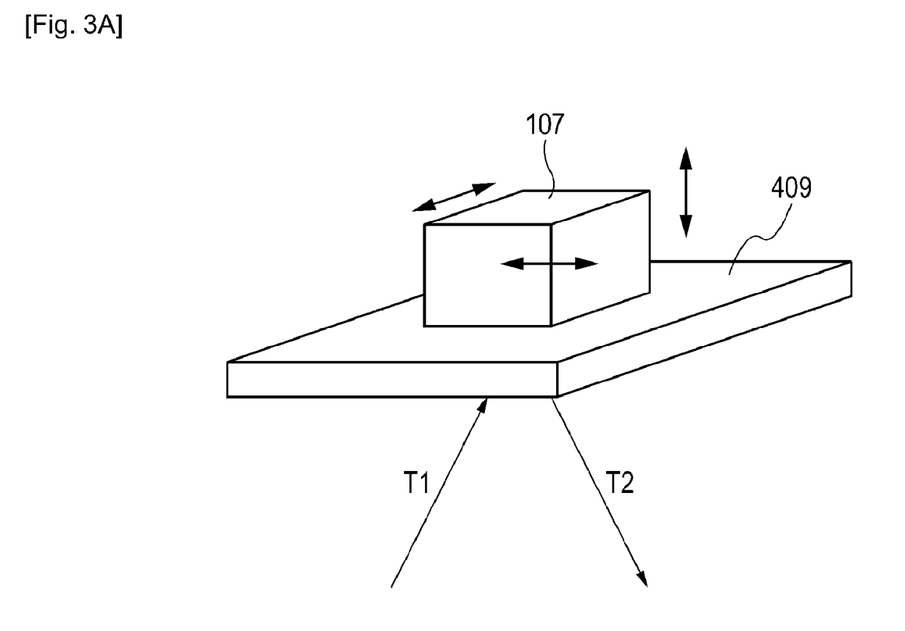
FIG. 3A is an illustration explaining an exemplary adjustment mechanism according to an embodiment.
Figure 3B:
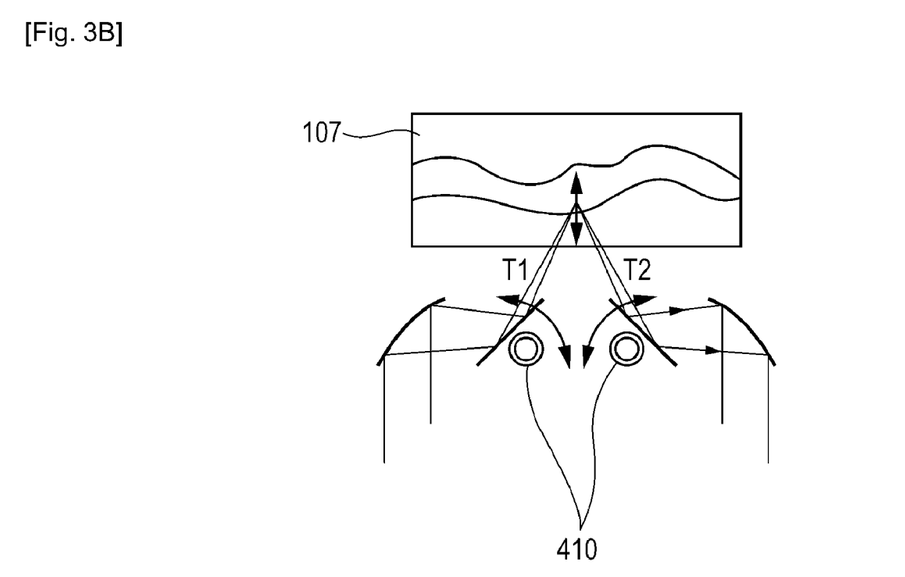
FIG. 3B is an illustration explaining an exemplary adjustment mechanism according to an embodiment.

To increase the versatility of the analyzing apparatus, the analyzing apparatus desirably includes an adjustment mechanism that adjusts the focal position. For example, as shown in FIG. 3A, the adjustment mechanism may have a configuration including a sample-moving stage 409 that moves the sample 107 relative to the terahertz wave pulse. Alternatively, as shown in FIG. 3B, the adjustment mechanism may have a configuration including a beam-scanning mechanism 410 that adjusts the reflection angles of the terahertz wave pulses T1 and T2. In particular, when the beam-scanning mechanism 410 is applied, the response of a terahertz wave pulse to a change in reflection angle is desirably checked in advance by using a sample, such as a flat plate coated with gold, which completely reflects a terahertz wave pulse. The focal position is adjusted within a range in which the response of the terahertz wave pulse is not changed.

Figure 4A:
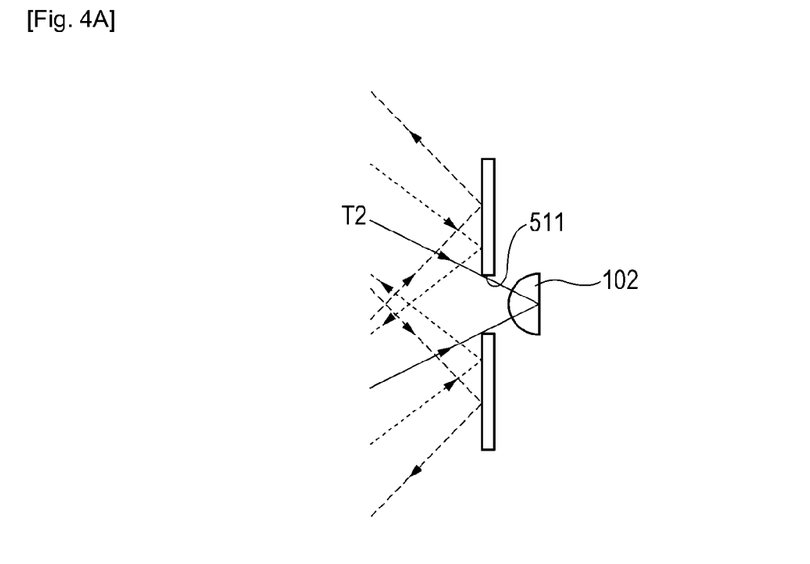
FIG. 4A is an illustration explaining other configuration according an embodiment.

As described above, the selection unit 106 uses the phenomenon in which the images from the positions other than the focal position are spread and formed, and selects the terahertz wave pulse reflected from the focal position in the sample 107. At this time, as shown in FIG. 4A, the analyzing apparatus according to this embodiment may have an opening 511 on the side where the terahertz wave pulse T2 is incident on the detection unit 102. With this configuration, the components other than the component from the focal position are prevented from being input to the detection unit 102, and a difference is generated between the signal intensity from a position other than the focal position and the signal intensity from the focal position. Thus, the terahertz wave from the focal position can be easily extracted.

The above described configuration is for the analyzing apparatus of this embodiment. Next, an analyzing apparatus and an analyzing method having a characteristic operation according to other embodiment will be described below.

Second Embodiment

An example operation of an analyzing apparatus and an analyzing method according to a second embodiment of the present invention will be described.

Figure 6A:
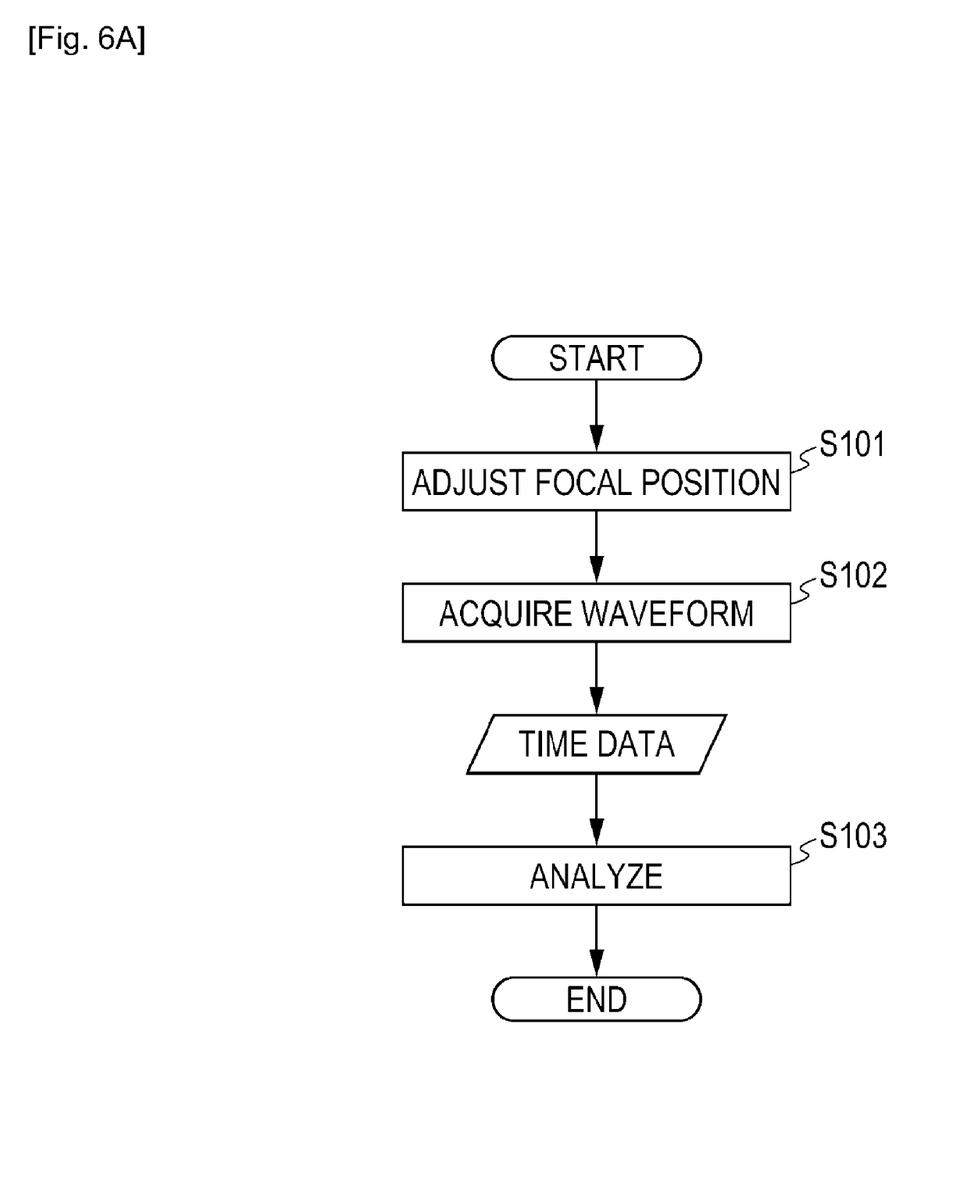
FIG. 6A is an operation flowchart for an analyzing apparatus and an analyzing method according to an embodiment.

FIG. 6A shows an operation flow of the analyzing apparatus according to this embodiment. When measurement is started, the analyzing apparatus adjusts the focal position in the sample 107 by using the adjustment mechanism (S101). The adjustment mechanism may perform manual adjust to a predetermined focal position, or automatic adjustment. If the inner structure of the sample 107 can be predicted, the focal position may be determined on the basis of the inner structure. The analyzing apparatus acquires a reflection time waveform of a terahertz wave pulse via the selection unit 106 while keeping the focal position fixed (S102). By using the acquired time waveform, the sample 107 is visualized. Also, by using the time waveform, the property of the sample 107 may be analyzed (S103). Referring to FIG. 1, if the focal position is on the interface B, the terahertz wave pulse reflected from the interface B is focused on the detection unit 102, whereas the terahertz wave pulses from the interfaces A and B are spread. Consequently, in the detection unit 102, the intensities of the terahertz wave pulses reflected from the interfaces A and C are smaller than the intensity of the pulse reflected from the interface B. FIG. 5A shows the time waveform constructed by the processing unit 105 when the selection unit 106 is not provided. If the terahertz wave pulse T2 reflected from the sample 107 passes through the selection unit 106, the time waveform of the terahertz wave pulse constructed by the processing unit 105 approaches to an isolated waveform as shown in FIG. 5B. Owing to this, in the frequency spectrum obtained by the analyzing apparatus according to this embodiment, the interference fringe is restricted although the plurality of reflected waves are present, and the analytical performance is increased.

Third Embodiment

Next, an example operation of an analyzing apparatus and an analyzing method according to a third embodiment of the present invention will be described. In particular, the third embodiment is a modification of the second embodiment, and relates to a method of acquiring a terahertz wave pulse. In this embodiment, the description of the part common to that in the former embodiments will be omitted.

The acquisition time for the time waveform of the terahertz wave pulse depends on the adjustment amount of the delay optical unit 103 shown in FIG. 1. The delay optical unit 103 adjusts the sampling position of the terahertz wave pulse. The acquisition time for the time waveform is determined on the basis of the adjustment range of the position. In the second embodiment, the start position and range of the acquisition time is fixed for the comparison between the case without the selection unit 106 (typical THz-TDS apparatus) and the case with the selection unit 106.

However, sufficient analysis may be difficult under the condition of the fixed acquisition time depending on the property and position of the interface of the sample 107. For example, when the measurement is ended before a vibration component due to the property of the interface B is settled, a time waveform in which the information of the interface B is not correctly reflected may be acquired. In this embodiment, to avoid such a situation, the measurement is performed during a predetermined period of time until the vibration component of the terahertz wave pulse selected for the focal position is attenuated. The predetermined period of time contains a period of time in which the vibration component of the selected terahertz wave pulse is attenuated and settled.

Figure 5C:
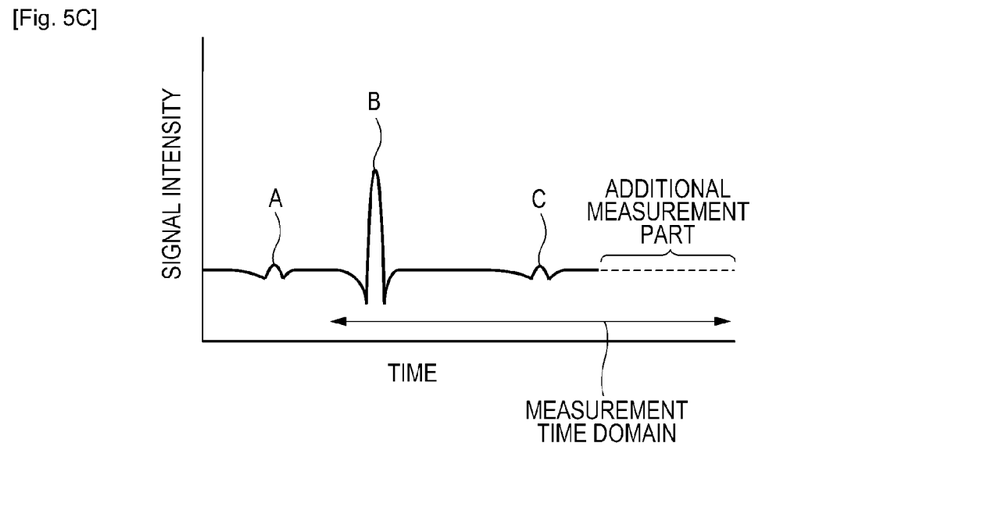
FIG. 5C is an illustration explaining an exemplary operation of a terahertz wave analyzing apparatus according to an embodiment.

In this embodiment, the predetermined period of time is a time domain with a predetermined length since the terahertz wave pulse is generated, the time domain containing at least the period of time in which the vibration component of the selected terahertz wave pulse is settled. The predetermined time domain is determined by an operator. For example, it is considered that a predetermined time domain for the measurement of the terahertz wave pulse reflected from the focal position on the interface A is a measurement time shown in FIG. 5A. At this time, if the terahertz wave reflected from the focal position on the interface B is measured in the same time domain, the measurement time may be insufficient. Thus, referring to FIG. 5C, an additional measurement part is set and then the same time domain is set. Describing a specific operation of the analyzing apparatus, the delay optical unit 103 controls the acquisition time range, from the sampling point at which the terahertz wave pulse is generated, to be constant. Also, the position of a window in the measurement time domain containing the terahertz wave pulse is shifted in accordance with the focal position in the sample. With this control, by fixing the measurement time domain, the resolutions for the frequency spectra of the properties at the different focal positions in the sample may easily become uniform. The reliability on comparison among a plurality of pieces of acquisition information can be increased.

Depending on the property at the focal position, the vibration component of the selected terahertz wave pulse may be attenuated and settled. In this case, an embodiment may be conceivable in which the predetermined period of time is a period of time until the vibration component of the selected terahertz wave pulse is attenuated by a predetermined amount with respect to a maximum amplitude of the selected terahertz wave pulse. The predetermined attenuation amount for the vibration component may be typically at least about −40 dB with respect to the maximum intensity of the terahertz wave pulse reflected from the focal position. If the predetermined amount is small (that is if the attenuation amount is insufficient), it is difficult to recognize the terahertz wave pulse as an isolated wave. Such setting may degrade reducing effect when, for example, averaging of a time waveform is applied to a method of reducing a noise floor of a frequency spectrum. With this control, the measurement time range can be adjusted in accordance with the attenuated state of the vibration component of the terahertz wave pulse. Thus, the measurement efficiency can be increased.

With this embodiment, the time waveform of the terahertz wave pulse that is changed depending on the property of the interface of the sample can be reliably acquired by adjusting the time domain in which the time waveform of the terahertz wave pulse is measured. Accordingly, increase in reliability of analysis can be expected.

Fourth Embodiment

An example operation of an analyzing apparatus and an analyzing method according to a fourth embodiment of the present invention will be described. In particular, the fourth embodiment is a modification of the second embodiment, and relates to a method of adjusting a focal position of a terahertz wave pulse. In this embodiment, the description of the part common to that in the former embodiments will be omitted.

In this embodiment, when the focal position is adjusted (S101) in FIG. 6A, a focal position is scanned in the sample, and the terahertz wave pulses from respective focal positions are monitored to determine a focal position. For scanning of the focal position, the adjustment mechanism is used. The delay optical unit 103 is adjusted such that the terahertz wave pulse is monitored in the measurement time domain containing about one cycle of the terahertz wave pulse. The focal position is adjusted (S101) with reference to information of the terahertz wave pulse corresponding to the focal position thus obtained.

As described above, the preliminary measurement is performed before the analysis of the sample 107, to determine the focal position. Accordingly, the terahertz wave pulse reflected from the predetermined focal position can be reliably analyzed. The working efficiency is increased.

Fifth Embodiment

An example operation of an analyzing apparatus and an analyzing method according to a fifth embodiment of the present invention will be described. In particular, the fifth embodiment is a modification of the second embodiment, and relates to a method of adjusting a focal position of a terahertz wave pulse. In this embodiment, the description of the part common to that in the former embodiments will be omitted.

Figure 6B:
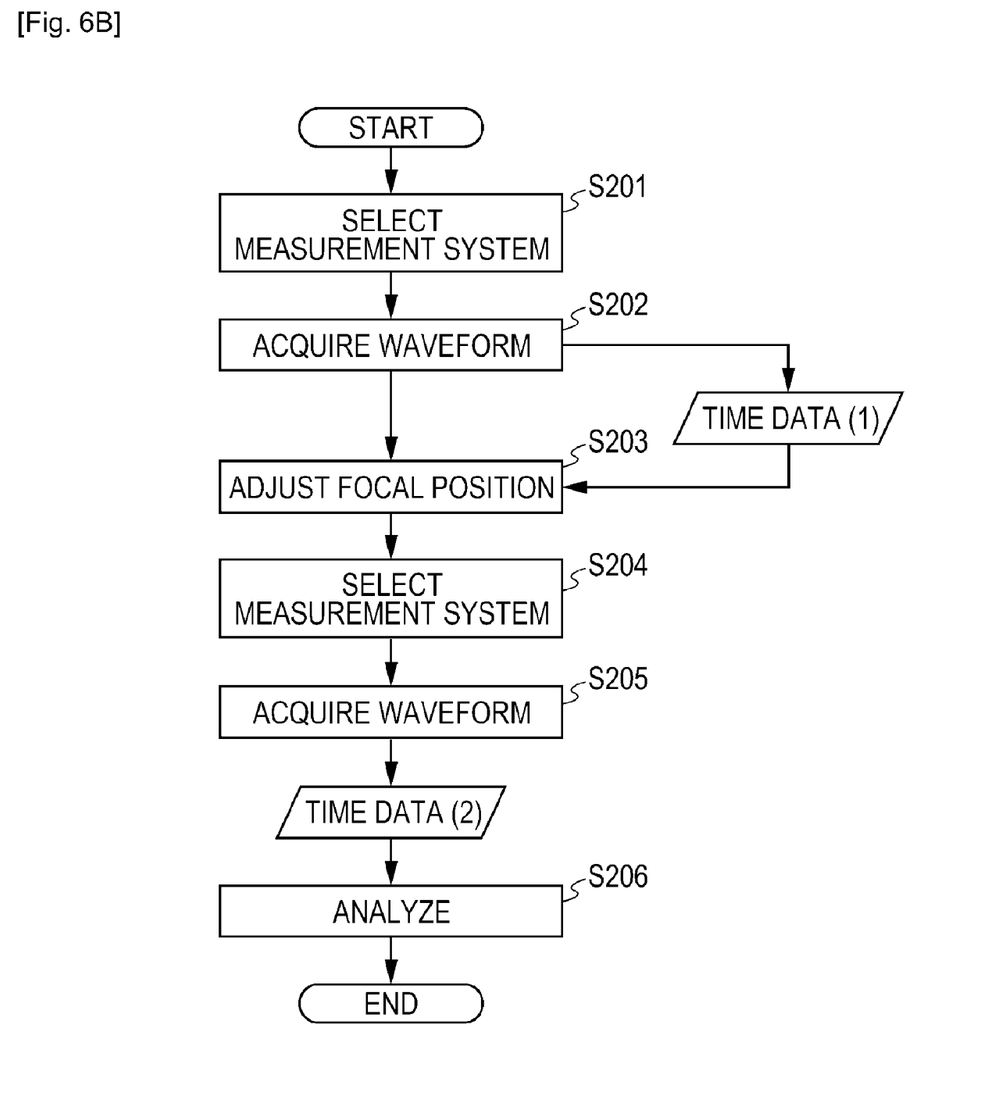
FIG. 6B is an operation flowchart for an analyzing apparatus and an analyzing method according to an embodiment.

FIG. 6B shows an operation flow of the analyzing apparatus according to this embodiment. This embodiment is different from the former embodiments in that, when a focal position is adjusted, a reflection waveform from an interface of the sample 107 is acquired once and an adjustment position is determined on the basis of the reflection waveform. Owing to this, referring to FIG. 4B, the analyzing apparatus includes a selection mechanism 612 that selects a measurement system.

Figure 4B:
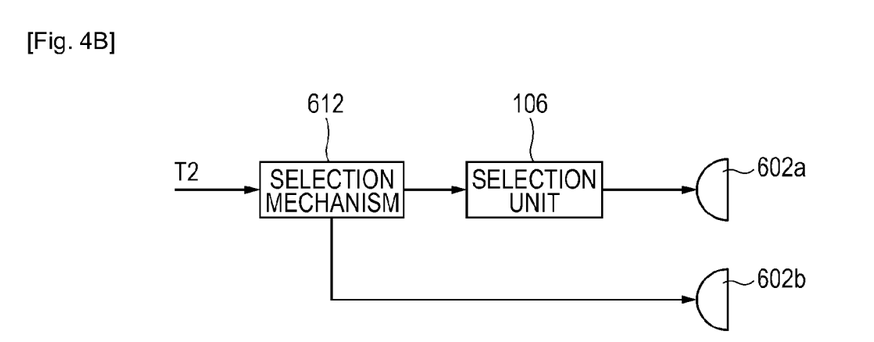
FIG. 4B is an illustration explaining other configuration according an embodiment.

The selection mechanism 612 has a function for switching a system between a measurement system including a selection unit 106 and a detection unit 602a, and a measurement system including a detection unit 602b. For example, the configuration of the selection mechanism 612 may be that a path through which a terahertz wave pulse propagates is optically switched by using an optical element such as a mirror. Alternatively, the configuration of the selection mechanism 612 may be that such two measurement systems are mechanically moved, and the measurement systems may be switched depending on the arrangement. When the measurement systems are switched depending on the arrangement, the detection units 602a and 602b may be common, and the selection unit 106 may be inserted to or removed from the propagation path of the terahertz wave pulse. In either case, the analyzing apparatus according to this embodiment may have any configuration as long as the reflection waveform of the interface in the sample 107 is acquired and the time waveform of the focal position is selected and acquired on the basis of the reflection waveform by using the selection mechanism 612.

Referring to FIG. 6B, when measurement is started, the analyzing apparatus selects the measurement system that can acquire the reflection waveform from the interface of the sample 107 (S201). In this state, the time waveform of the terahertz wave pulse reflected from the sample 107, the pulse which does not pass through the selection unit 106, is measured (S202). If the inner structure of the sample 107 has the interfaces A, B, and C as shown in FIG. 1, the time waveform that is measured in this process becomes a waveform shown in FIG. 5A. The reflection pulses shown in FIG. 5A correspond to the respective interfaces. The analyzing apparatus determines the focal position and adjusts the focal position in accordance with data (1) of the time waveform (S203).

Then, the analyzing apparatus changes the measurement system such that the terahertz wave reflected from the sample 107 passes through the selection unit 106 (S204). At this time, when the optical path length from the sample 107 to the detection unit 602b is changed as a result of the selection of the measurement system, the analyzing apparatus also adjusts the delay optical unit 103. In this state, the analyzing apparatus measures the terahertz wave pulse selected depending on the focal position (S205 to S206).

By determining the focal position from the reflection waveform reflected from the interface in the sample 107, the analyzing apparatus can reliably analyze the terahertz wave pulse reflected from the focal position. The working efficiency is increased.

Sixth Embodiment

An apparatus and a method according to a sixth embodiment will be described. In this embodiment, the above-described analyzing apparatus is used as an image acquiring apparatus. The description of the part common to that in the former embodiments will be omitted.

The above-described analyzing apparatus measures and analyzes the time waveform of the terahertz wave pulse from the focal position. When the analyzing apparatus is used as the image acquiring apparatus, the image acquiring apparatus scans a focal position, and plots terahertz wave pulses from respective focal positions in the sample to acquire an image of the sample.

An operation of the image acquiring apparatus will be described. In this embodiment, in a scanning range of the focal position, the shape of the interface in the sample 107 is changed within a region in which a focal point is attained.

Figure 7A:
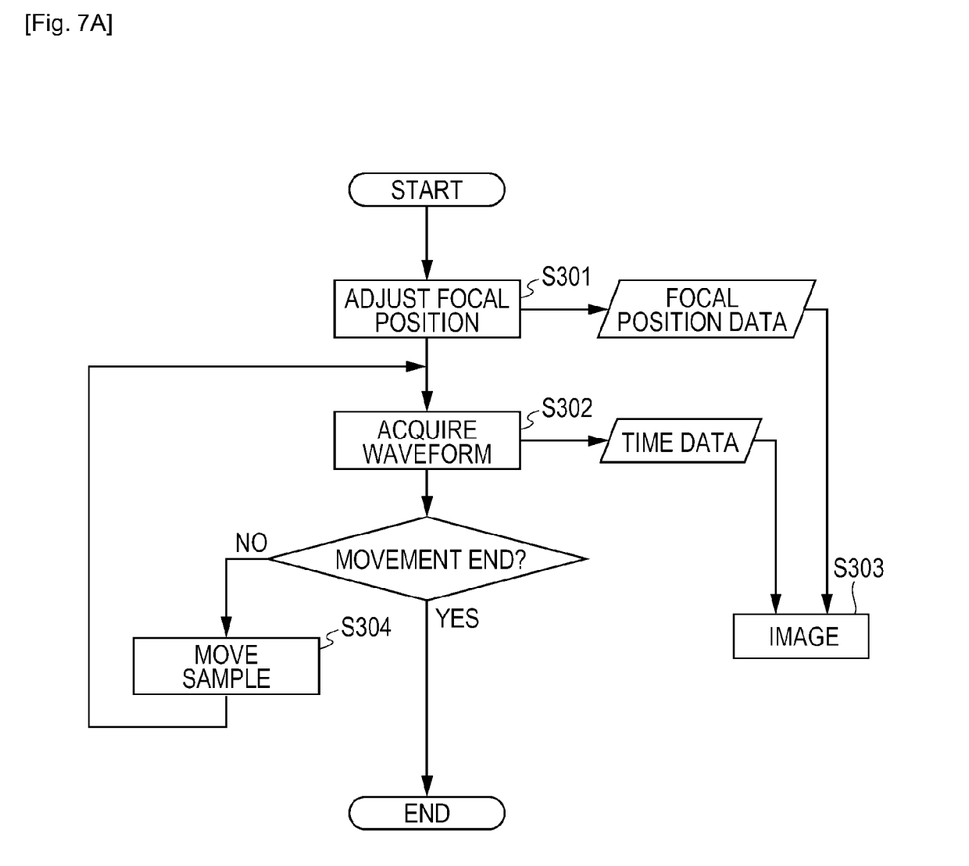
FIG. 7A is an operation flowchart for an image acquiring apparatus and an image acquiring method according to an embodiment.

FIG. 7A shows an operation flow of the image acquiring apparatus according to this embodiment. In FIG. 7A, when the image acquiring apparatus starts the measurement, the image acquiring apparatus adjusts the focal position to an interface to be measured from among interfaces of the sample 107 (S301). For example, the focal position is adjusted to the interface B in the sample 107 in FIG. 1. Then, the image acquiring apparatus measures the time waveform of the terahertz wave pulse reflected from the focal position (S302). The processing unit 105 performs visualization. Herein, a positional change on a time base of the terahertz wave pulse is plotted, and the structure of the interface is visualized. The processing unit 105 stores the position on the time base of the terahertz wave pulse for the current focal position (S303).

Next, scanning of the focal position is performed. In this embodiment, the focal position is scanned by movement of a sample. For example, the sample 107 shown in FIG. 1 is moved in a direction in which an interface extends (S304). The method of scanning of the focal position is not limited to the above method as long as the focal position is moved relative to the sample 107.

After the sample 107 is moved to a desirable position, the terahertz wave pulse reflected from the focal position is measured again, and the position on the time base of the terahertz wave pulse is recorded (S302 to S303).

When scanning of the focal position is ended, the operation of the image acquiring apparatus is ended. With such a procedure, by associating the focal position with the positional change on the time base of the terahertz wave pulse, the structure of the interface can be visualized. In this embodiment, the positional change on the time base of the terahertz wave pulse is used; however, the visualizing method is not limited thereto. For example, the position at which a predetermined time waveform is present in a time waveform of a terahertz wave pulse that changes depending on the property of the interface is plotted, and visualization of the interface may be performed with analysis. Alternatively, a frequency spectrum may be calculated on the basis of the time waveform of the terahertz wave, and visualization may be performed for every frequency. Still alternatively, a material or a property may be acquired from a frequency spectrum, and a distribution thereof on an interface may be visualized.

According to this embodiment, for example, an image of a specific interface is selected and visualized as compared with a method of deriving an image of a desirable interface from images with a plurality of levels mixed. Accordingly, image information of the specific interface can be easily recognized.

Seventh Embodiment

An apparatus and a method according to a seventh embodiment will be described. In this embodiment, the above-described analyzing apparatus is used as an image acquiring apparatus. In particular, the seventh embodiment is a modification of the sixth embodiment. The description of the part common to that in the former embodiments will be omitted.

In the image acquiring apparatus in the sixth embodiment, the shape of the interface in the sample 107 changes within the region in which the focal point is attained, in a range for scanning the focal position. In the seventh embodiment, visualization of information of an interface exceeding the range in which a focal point is attained can be performed. Hence, in this embodiment, a process is additionally provided for adjusting again the focal position if the position of the interface tends to exceed the region in which a focal point is attained.

Figure 7B:
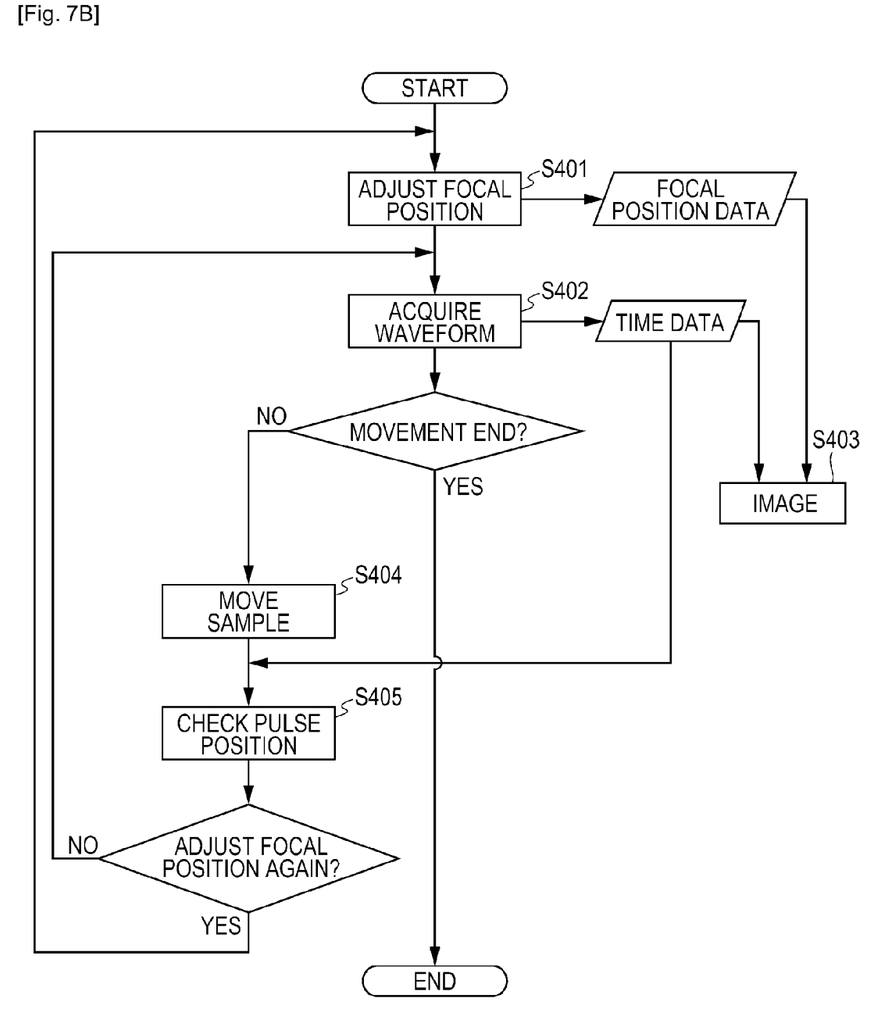
FIG. 7B is an operation flowchart for an image acquiring apparatus and an image acquiring method according to an embodiment.

FIG. 7B shows an operation flow of an image acquiring apparatus according to this embodiment. When the image acquiring apparatus starts measurement, the image acquiring apparatus adjusts the focal position by the adjustment mechanism (S401), and plots the change in time waveform of the terahertz wave pulse as a result of the focal position being scanned (S402 to S404).

Herein, the apparatus monitors a change in position of the time waveform of the terahertz wave pulse obtained when the focal position is adjusted (S405). If it is determined that the changed position exceeds the region in which a focal point is attained, the apparatus adjusts the focal position again (S401). For visualization, visualizing is performed by taking into account the adjustment amount of the focal position and the changed position of the time waveform. The adjustment of the focal position is properly adjusted. Accordingly, the apparatus tracks the rough structure of the interface. Thus, with information of the changed position of the time waveform, the fine structure of the interface is extracted from the rough structure.

Such an operation is repeated within the scanning range of the focal position.

With this embodiment, by combining the adjustment amount of the adjustment mechanism with information of the time by which the pulse is generated in the time waveform, the region in which visualization is available can extend. Information of the inside of a larger structure body can be easily visualized. Also, while visualization is performed during tracking of the interface, visualization of information of a more complex interface can be easily performed.

Eighth Embodiment

An apparatus and a method according to an eighth embodiment will be described. In this embodiment, the above-described analyzing apparatus is used as an image acquiring apparatus. The description of the part common to that in the former embodiments will be omitted.

Figure 4C:
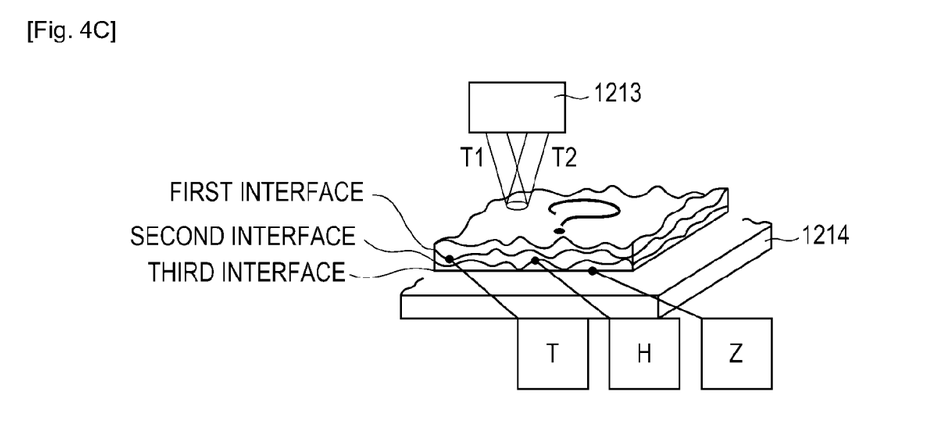
FIG. 4C is an illustration explaining other configuration according an embodiment.

FIG. 4C is a brief configuration diagram of an image analyzing apparatus according to this embodiment. In FIG. 4C, a sample is a painting in which pigments are layered on one another. The boundaries of the layers define interfaces. On the interfaces of the painting, characters of "T (first interface)", "H (second interface)", and "Z (third interface)" are drawn with a pigment (P) having special absorption for at least a terahertz wave band. The sample is arranged on a scanning mechanism 1214. An image acquiring apparatus 1213 is the above-described apparatus. A predetermined focal position in the sample is irradiated with a terahertz wave pulse T1, and a terahertz wave pulse T2 reflected from the focal position is measured. The scanning mechanism 1214 has a function of adjusting and scanning the focal position.

In a measurement device for a terahertz wave of related art, when an image of a sample is acquired, images of respective interfaces are overlapped and visualized, and hence characters drawn with the pigment (P) are also overlapped. Thus, it is necessary to find images corresponding to the images of the respective interfaces by post processing. With the apparatus of this embodiment, for example, the focal position is adjusted to be located on the first interface, and the information of the interface can be visualized. Thus, the information "T" with the pigment (P) can be extracted because of the difference in property, and the information of the character "T" can be read. The focal position is successively adjusted to be located on the second and third positions. Thus, the characters "H" and "Z" can be read.

This embodiment describes the example for acquiring information drawn with a certain pigment in a painting. However, an application example is not limited thereto. For example, the configuration of this embodiment can be applied to an apparatus that reads information of a certain page from layered sheets of paper, such as a book. Alternatively, the configuration of this embodiment can be applied to an apparatus that inspects the state of a paint, which is for coating an object, when the paint is located in a certain layer. That is, the configuration of this embodiment can be applied to a general apparatus that acquires information of a certain interface from an object in which interfaces are layered.

With this embodiment, image information of a certain interface can be easily analyzed. Thus, versatility is increased.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-012455, filed Jan. 23, 2009, and No. 2009-288818, filed Dec. 21, 2009, which are hereby incorporated by reference herein in their entirety.

The invention claimed is:

1. An analyzing apparatus configured to analyze an object by using a terahertz wave, the analyzing apparatus comprising:
   a generation unit configured to generate the terahertz wave;
   a detection unit configured to detect the terahertz wave;
   a first optical unit configured to cause the terahertz wave generated by the generation unit to be condensed at a first position in the object;
   a selection unit configured to cause the terahertz wave from the object to be condensed on a detection surface of the detection unit,
   wherein the selection unit includes
      a second optical unit configured to cause the terahertz wave from the object to be condensed at a second position, and
      a third optical unit configured to cause the terahertz wave condensed at the second position to be condensed at a third position on the detection surface; and
   wherein the selection unit has more focal points than the first optical unit.

2. The analyzing apparatus according to claim 1, wherein the detection unit is a photoconductive element including a photoconductive film and a pair of electrodes provided in the photoconductive film with a gap interposed therebetween, and
   wherein the third position is located in the gap to be located on a surface of the photoconductive film in which the pair of electrodes are provided.

3. The analyzing apparatus according to claim 1, further comprising a time waveform acquiring unit configured to, by using terahertz time domain spectroscopy, acquire a time waveform of the terahertz wave reflected from the first position in the object with the terahertz wave detected by the detection unit.

4. The analyzing apparatus according to claim 3, further comprising:
   a delay optical unit configured to change a timing at which the terahertz wave is detected; and
   a control unit configured to control the delay optical unit on the basis of a time domain of the time waveform,
   wherein the time domain is set in accordance with an intensity of the terahertz wave detected by the detection unit.

5. The analyzing apparatus according to claim 1, wherein an opening is arranged between the third optical unit and the detection unit, the opening being arranged to allow the terahertz wave condensed at the third position from the object to pass through the opening selectively from among the terahertz waves from the object.

* * * * *